(12) United States Patent
Copland et al.

(10) Patent No.: US 9,468,369 B2
(45) Date of Patent: Oct. 18, 2016

(54) MODEL EYE PRODUCING A SPECKLE PATTERN HAVING A REDUCED BRIGHT-TO-DARK RATIO FOR USE WITH OPTICAL MEASUREMENT SYSTEM FOR CATARACT DIAGNOSTICS

(71) Applicant: AMO WaveFront Sciences, LLC., Albuquerque, NM (US)

(72) Inventors: Richard J. Copland, Albuquerque, NM (US); Daniel R. Neal, Tijeras, NM (US); Thomas D. Raymond, Edgewood, NM (US); Wei Xiong, Albuquerque, NM (US); Paul D. Pulaski, Albuquerque, NM (US); Stephen W. Farrer, Albuquerque, NM (US); Carmen Canovas Vidal, Groningen (NL); Daniel R. Hamrick, Cedar Crest, NM (US)

(73) Assignee: AMO WaveFront Sciences, LLC, Albuquerque, NM (US)

( * ) Notice: Subject to any disclaimer, the term of this patent is extended or adjusted under 35 U.S.C. 154(b) by 8 days.

(21) Appl. No.: 14/559,667

(22) Filed: Dec. 3, 2014

(65) Prior Publication Data
US 2015/0131053 A1    May 14, 2015

Related U.S. Application Data

(60) Continuation-in-part of application No. 13/950,756, filed on Jul. 25, 2013, now Pat. No. 8,919,956, which is a division of application No. 13/011,003, filed on Jan. 21, 2011, now Pat. No. 8,517,538.

(51) Int. Cl.
*A61B 3/10*     (2006.01)
*A61B 3/14*     (2006.01)
(Continued)

(52) U.S. Cl.
CPC ............. *A61B 3/0025* (2013.01); *A61B 3/102* (2013.01); *A61B 3/1005* (2013.01); *A61B 3/107* (2013.01);
(Continued)

(58) Field of Classification Search
CPC .... A61B 3/00; A61B 3/0025; A61B 3/1015; A61B 3/1005; A61B 3/102; A61B 3/107; A61B 3/117; A61B 2017/00716; A61B 2560/0233; A61B 5/0066; A61F 2/14; A61F 2/141; A61F 2/142; A61F 2/16; A61F 2/1613; G02B 27/48
USPC ................ 351/204–206, 208, 212, 221, 246; 623/6.11
See application file for complete search history.

(56) References Cited

U.S. PATENT DOCUMENTS

| | | |
|---|---|---|
| 1,630,944 A | 5/1927 | Ingersoll |
| 2,068,950 A | 1/1937 | Frederick |

(Continued)

FOREIGN PATENT DOCUMENTS

| | | |
|---|---|---|
| DE | 102006025638 A1 | 12/2007 |
| DE | 102008055755 A1 | 5/2010 |

(Continued)

OTHER PUBLICATIONS

International Search Report and Written Opinion for Application No. PCT/US2014/068412, mailed Mar. 9, 2015, 10 pages.

(Continued)

*Primary Examiner* — Loha Ben
(74) *Attorney, Agent, or Firm* — Abbott Medical Optics Inc.

(57) ABSTRACT

A system includes a model eye and an optical measurement instrument, which includes: a corneal topography subsystem; a wavefront sensor subsystem; and an eye structure imaging subsystem. The subsystems may have a common fixation axis, and be operatively coupled to each other via a controller. The optical measurement instrument may perform measurements of the model eye to verify correct operation of the optical measurement instrument for measuring one or more characteristics of a subject's eye. The model eye may include an optically transmissive structure having a front curved surface and an opposite rear planar surface, and a material structure provided at the rear planar surface of the optically transmissive structure and having a characteristic to cause a speckle pattern of a portion of a coherent light beam that is directed back out the front curved surface of the optically transmissive structure to have a bright-to-dark ratio of less than 2:1.

30 Claims, 11 Drawing Sheets

(51) Int. Cl.
*A61B 3/00* (2006.01)
*A61B 3/107* (2006.01)
*G02B 27/48* (2006.01)
*A61F 2/14* (2006.01)
*A61F 2/16* (2006.01)
*A61B 17/00* (2006.01)
*A61B 5/00* (2006.01)

(52) U.S. Cl.
CPC ............. *A61B 3/1015* (2013.01); *G02B 27/48* (2013.01); *A61B 5/0066* (2013.01); *A61B 2017/00716* (2013.01); *A61B 2560/0233* (2013.01); *A61F 2/14* (2013.01); *A61F 2/142* (2013.01); *A61F 2/16* (2013.01)

(56) References Cited

U.S. PATENT DOCUMENTS

| | | | |
|---|---|---|---|
| 3,598,470 | A | 8/1971 | Vetter |
| 4,009,394 | A | 2/1977 | Mierzwinski |
| 4,253,743 | A | 3/1981 | Matsumura |
| 5,042,938 | A | 8/1991 | Shimozono |
| 6,485,142 | B1 | 11/2002 | Sheehy et al. |
| 6,626,535 | B2 | 9/2003 | Altmann |
| 6,705,729 | B2 * | 3/2004 | Piers ............... A61B 3/1015 351/246 |
| 6,802,609 | B2 | 10/2004 | Mihashi et al. |
| 7,036,933 | B2 * | 5/2006 | Yamaguchi ............ A61B 3/00 351/205 |
| 7,425,067 | B2 | 9/2008 | Warden et al. |
| 7,546,009 | B2 | 6/2009 | Kukulj et al. |
| 7,742,244 | B2 | 6/2010 | Liu et al. |
| 7,792,249 | B2 | 9/2010 | Gertner et al. |
| 7,878,655 | B2 * | 2/2011 | Salvati ............... A61B 3/0025 351/221 |
| 8,128,228 | B2 * | 3/2012 | Van Heugten ....... A61B 3/1005 351/204 |
| 8,128,262 | B2 | 3/2012 | Ramer et al. |
| 8,686,648 | B2 | 4/2014 | Ramer et al. |
| 2002/0041359 | A1 | 4/2002 | Mihashi et al. |
| 2003/0025877 | A1 | 2/2003 | Yancey et al. |
| 2003/0174755 | A1 | 9/2003 | Lai et al. |
| 2009/0251664 | A1 | 10/2009 | Norrby et al. |
| 2010/0002311 | A1 | 1/2010 | Reichert |
| 2011/0181836 | A1 | 7/2011 | Rowe |

FOREIGN PATENT DOCUMENTS

| | | |
|---|---|---|
| WO | WO-03049606 A2 | 6/2003 |
| WO | WO-2005047938 A2 | 5/2005 |
| WO | WO-2010086304 A1 | 8/2010 |
| WO | WO-2012100129 A2 | 7/2012 |

OTHER PUBLICATIONS

International Search Report for Application No. PCT/US2012/021979, mailed on Sep. 4, 2012, 6 pages.

* cited by examiner

MODEL EYE PRODUCING A SPECKLE PATTERN HAVING A REDUCED BRIGHT-TO-DARK RATIO FOR USE WITH OPTICAL MEASUREMENT SYSTEM FOR CATARACT DIAGNOSTICS

CROSS-REFERENCES TO RELATED APPLICATIONS

This patent application is a continuation-in-part of U.S. patent application Ser. No. 13/950,756, filed on 25 Jul. 2013, now U.S. Pat. No. 8,919,956, which is in turn a divisional of U.S. patent application Ser. No. 13/011,003, filed 21 Jan. 2011 and issued as U.S. Pat. No. 8,517,538, the entire contents of all of which are incorporated herein by reference.

TECHNICAL FIELD

Embodiments of this invention pertain to optical measurement equipment, and more particularly, to a model eye for verifying proper operation and performance of optical measurement equipment, including an optical measurement instrument for carrying out cataract diagnostics, and a method for verifying proper operation and performance of such optical measurement equipment with a model eye.

BACKGROUND

A number of optical measurement or analysis instruments use one or more light spots generated from coherent light sources, such as lasers or superluminescent diode (SLDs), to make optical measurements of the eye. Well-known examples of such instruments include wavefront aberrometers (e.g., Shack-Hartmann wavefront aberrometers), corneal topographers, as well as optical coherence tomographers. A new class of combined instruments is also emerging for performing comprehensive eye measurements for refractive errors and/or for carrying out diagnostic measurements and analysis for cataract procedures, including for example, intraocular lens placement and alignment.

An undesirable feature of the light sources used in some of these instruments is that the light pattern produced in the instrument is marred by speckle. Speckle is a spotty pattern with large light intensity variations. FIG. 1 illustrates an example of a speckle pattern. Speckle is caused when the layer from which the light is scattered is thinner than the coherence length of the light source. A typical SLD has a bandwidth of thirty nanometers, which corresponds to a coherence length of one hundred microns.

Speckle can cause problems with some optical measurement or analysis instruments. For example, there are two ways that speckle causes measurement errors in an instrument that employs a Shack-Hartmann wavefront sensor. One problem is that the mathematical algorithms called reconstructors that are employed by such instruments have fitting errors in data sets that contain dark regions of the speckle pattern. Another problem is "intensity coupling." Intensity coupling may occur when a wavefront sensor is constructed such that the lenslet array is not located exactly one focal length from the pixel array. In that case, intensity variations cause shifts in the spot locations that are independent of the slope of the wavefront. These shifts cause errors in the calculated wavefront.

With the human eye, speckle is mitigated because the scattering occurs in a volume that has a thickness that is longer than the coherence length of the light source. The light penetrates into a layer of the eye and weak scatter occurs throughout the volume. As a result, when an SLD light source illuminates a human eye, the bright to dark ratio is typically about two to one.

Meanwhile, it is sometimes necessary to be able to verify correct operation and specified performance of an optical measurement instrument such as those described above in an operational setting. In many instances, this is done by operating the measurement instrument to make a measurement of a model eye whose characteristics are known. In that case, typically the optical measurement instrument injects a probe beam into a front surface of the model eye. Light scatters from the back surface of the model eye similarly to the way it does with a human eye, and some of the scattered light travels back out of the front surface and into the optical measurement instrument.

When a typical model eye is measured, however, the speckle is more severe than that typically seen when measuring a human eye. The problem is further exacerbated by the fact that the "cornea" of the model eye acts like a magnifying glass and makes the structure of the bright spots and dark regions appear large on the detector inside the optical measurement instrument. The typical speckle pattern for a model eye has a bright to dark ratio of twenty-to-one, which is about an order of magnitude greater than that of a speckle pattern for a human eye. For all these reasons, these large variations in light level cause inaccurate measurements that can in turn affect diagnosis and treatment.

Therefore, an improved model eye and systems and methods employing the same are desired.

SUMMARY OF THE INVENTION

Hence, to obviate one or more problems due to limitations and disadvantages of the related art, this disclosure provides embodiments for a model eye which produces a speckle pattern exhibiting a reduced bright-to-dark ratio. The disclosure further describes embodiments for a system and method for cataract diagnostics that employ such a model eye to verify correct and/or accurate performance of an optical measurement instrument employed for such diagnostics.

In one aspect of the invention, a method comprises: providing a model eye comprising an optically transmissive structure having a front curved surface and an opposite rear planar surface, and a material structure provided at the rear planar surface of the optically transmissive structure having a characteristic to cause a speckle pattern of a portion of a coherent light beam that is directed back out through the front curved surface of the optically transmissive structure to have a bright-to-dark ratio of less than 2:1; performing one or more measurements of the model eye to verify correct operation of an optical measurement instrument which includes: a corneal topography subsystem; a wavefront sensor subsystem; and an eye structure imaging subsystem; and employing the optical measurement instrument to measure a plurality of characteristics of a subject's eye, comprising ocular biometry information, anterior corneal surface information, posterior corneal surface information, anterior lens surface information, posterior lens surface information, lens tilt information and lens position information.

In some embodiments, the eye structure imaging subsystem comprises an optical coherence tomographer subsystem, and performing one or more measurements of the model eye to verify correct operation of the optical measurement instrument includes: performing an optical coherence tomography measurement, with the optical coherence tomography subsystem, to measure a thickness of the material structure provided at the rear planar surface of the optically transmissive structure of the model eye; comparing the measured thickness to a known thickness of the material structure provided at the rear planar surface of the optically transmissive structure of the model eye; and when the measured thickness does not agree with the known thickness within a particular tolerance, determining that the optical measurement instrument is not operating properly within specifications.

In some embodiments, the material structure comprises a fabric-reinforced polyethylene pressure-sensitive tape adhered to the rear planar surface of the optically transmissive structure by an adhesive.

In some embodiments, the material structure comprises at least two layers of optically transmissive adhesive tape with a material having a plurality of light scattering particles disposed between the at least two layers of optically transmissive adhesive tape.

In some embodiments, the material structure comprises a plurality of layers of optically transmissive adhesive tape with a plurality of pencil marks on each successive layer of the optically transmissive adhesive tape.

In some embodiments, the material structure comprises a layer of optically transmissive paint with light scattering particles embedded within.

In some embodiments, the material structure comprises a caulking material with a gauze material applied thereto.

In some embodiments, the method further comprises: determining a desired postoperative condition of the subject's eye; empirically calculating a post-operative condition of the eye based at least partially on the measured eye characteristics; and predictively estimating, in accordance with an output of said empirically calculating and the eye characteristics, at least one parameter of an intraocular lens for implantation into the subject's eye to obtain the desired postoperative condition.

In some embodiments, the ocular biometry information comprises a plurality of central corneal thicknesses (CCT), an anterior chamber depth (ACT), a pupil diameter (PD), a white to white distance (WTW), a lens thickness (LT), an axial length (AL) and a retinal layer thickness.

In some embodiments, the method further comprises: accessing a plurality of Intraocular Lens (IOL) models stored in a memory accessible by the optical measurement instrument, each of the IOL models having associated with it a plurality of predetermined parameters selected from the group consisting of dioptic power, refractive index, asphericity, toricity, haptic angulation and lens filter; and for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL from the plurality of IOL models corresponding to the optimized IOL based on a predetermined criteria.

In some embodiments, the material structure provided at the rear planar surface of the optically transmissive structure of the model eye has a plurality of layers, the eye structure imaging subsystem comprises an optical coherence tomographer subsystem, and performing one or more measurements of the model eye to verify correct operation of the optical measurement instrument includes: performing an optical coherence tomography measurement, with the optical coherence tomography subsystem, to measure thicknesses of at least two of the layers of the material structure provided at the rear planar surface of the optically transmissive structure of the model eye; comparing the measured thicknesses to known thicknesses of the at least two layers of the material structure provided at the rear planar surface of the optically transmissive structure of the model eye; and when the measured thicknesses for the at least two layers do not agree with the known thicknesses of the at least two layers within a particular tolerance, determining that the optical measurement instrument is not operating properly within specifications.

In another aspect of the invention, a system comprises: a model eye and an optical measurement instrument, The model eye comprises: an optically transmissive structure having a front curved surface and an opposite rear planar surface, and a material structure provided at the rear planar surface of the optically transmissive structure and having a characteristic to cause a speckle pattern of a portion of a coherent light beam that is directed back out the front curved surface of the optically transmissive structure to have a bright-to-dark ratio of less than 2:1. The optical measurement instrument includes: a corneal topography subsystem; a wavefront sensor subsystem; and an eye structure imaging subsystem, wherein the subsystems have a common fixation axis, and each subsystem is operatively coupled to the others via a controller, and wherein the optical measurement instrument is configured to perform one or more measurements of the model eye to verify correct operation of the optical measurement instrument for measuring one or more characteristics of a subject's eye.

In some embodiments, the material structure comprises a fabric-reinforced polyethylene pressure-sensitive tape adhered to the rear planar surface of the optically transmissive structure by an adhesive.

In some embodiments, the material structure comprises at least two layers of optically transmissive adhesive tape with a material having a plurality of light scattering particles disposed between the at least two layers of optically transmissive adhesive tape.

In some embodiments, the material structure comprises a plurality of layers of optically transmissive adhesive tape with a plurality of pencil marks on each successive layer of the optically transmissive adhesive tape.

In some embodiments, the material structure comprises a layer of optically transmissive paint with light scattering particles embedded within.

In some embodiments, the material structure comprises a caulking material with a cloth material applied thereto.

In some embodiments, the eye structure imaging subsystem is an optical coherence tomography subsystem.

In some embodiments, the optical coherence tomography subsystem is configured to perform an optical coherence tomography measurement to measure a thickness of the material structure provided at the rear planar surface of the optically transmissive structure of the model eye; and the controller is configured to compare the measured thickness to a known thickness of the material structure provided at the rear planar surface of the optically transmissive structure of the model eye, and when the measured thickness does not agree with the known thickness within a specified tolerance, determine that the optical measurement instrument is not operating properly within specifications.

In some embodiments, the system further comprises a memory operable to store data acquired from each of the corneal topography subsystem, the wavefront sensor subsystem and the eye structure imaging subsystem, wherein the stored data includes a plurality of ocular biometry information, anterior corneal surface information, posterior corneal surface information, anterior lens surface information, and posterior lens surface information, lens tilt information and lens position information.

In some embodiments, the system further comprises a memory operable to store intraocular lens (IOL) model data for a plurality of IOL models, each of the IOL models having associated with it a plurality of predetermined parameters selected from the group consisting of dioptic power, refractive index, asphericity, toricity, haptic angulation and lens filter.

In some embodiments, the system further comprises a processor configured to execute an algorithm. The algorithm comprises, for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL from the plurality of IOL models corresponding to the optimized IOL based on a predetermined criteria.

In some embodiments the system further comprises a processor configured to execute an algorithm. The algorithm comprises: determining a desired postoperative condition of the subject's eye; empirically calculating a post-operative condition of the subject's eye based at least partially on the one or more measured characteristics of the subject's eye; and predictively estimating, in accordance with an output of said empirically calculating and the eye characteristics, at least one parameter of an intraocular lens for implantation into the subject's eye to obtain the desired postoperative condition.

In yet another aspect of the invention, a system comprises: a model eye and an optical measurement instrument. The model eye comprises: an optically transmissive structure having a front curved surface and an opposite rear planar surface, and a tape adhered to the rear planar surface of the optically transmissive structure by a pressure sensitive adhesive. The optical measurement instrument includes: a corneal topography subsystem; a wavefront sensor subsystem; and an eye structure imaging subsystem, wherein the subsystems have a common fixation axis, and each subsystem is operatively coupled to the others via a controller, and wherein the optical measurement instrument is configured to perform one or more measurements of the model eye to verify correct operation of the optical measurement instrument for measuring one or more characteristics of a subject's eye.

In some embodiments, the model eye further comprises an opaque structure having an aperture therethrough disposed on an opposite side of the front curved surface of the optically transmissive structure as the rear planar surface of the optically transmissive structure.

In some embodiments, the optically transmissive structure comprises glass or a transparent polymer.

In some embodiments, the tape comprises a fabric-reinforced polyethylene tape with a pressure-sensitive adhesive.

In some embodiments, the tape comprises one of duct tape, gaffer tape, and a latex tape.

In some embodiments, the model eye further comprises a holder having an opening therein defining a sleeve configured to hold the optically transmissive structure.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

DETAILED DESCRIPTION

Exemplary embodiments of model eyes and methods for verifying proper operation and performance of optical measurement equipment through use of a model eye will be described in some detail below so as to illustrate various aspects and advantages of these devices and methods. However, it should be understood that the principles involved in these devices and methods can be employed in a variety of other contexts, and therefore the novel devices and method disclosed and claimed here should not be construed as being limited to the example embodiments described below.

Figure 1:
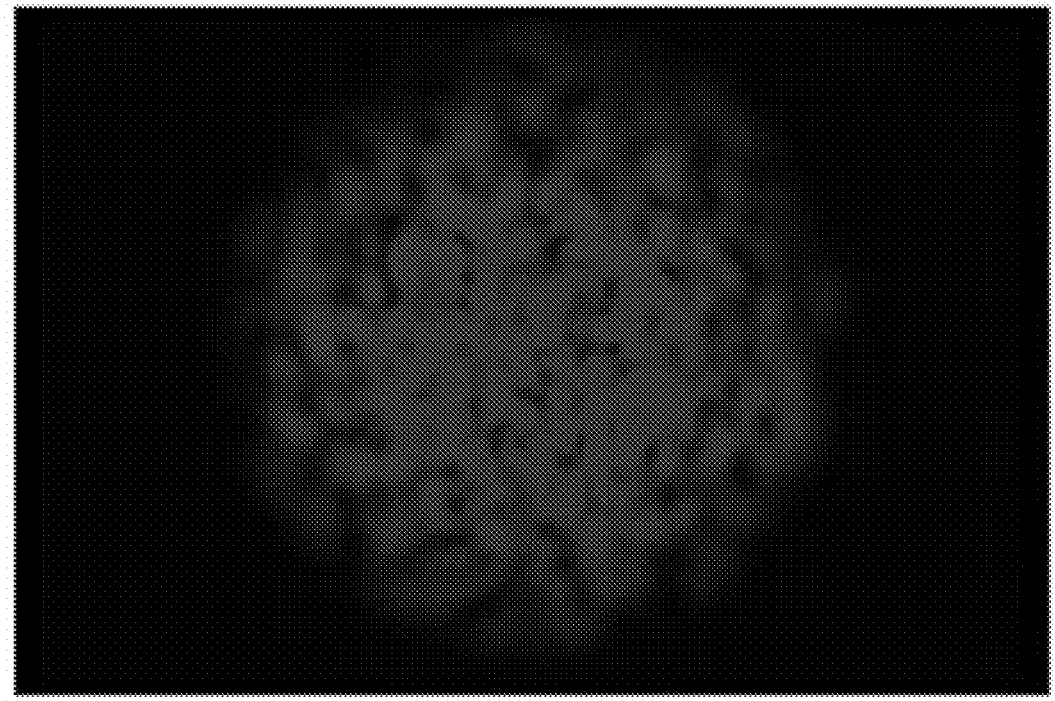
FIG. 1 illustrates an example of a speckle pattern.
Figure 2:
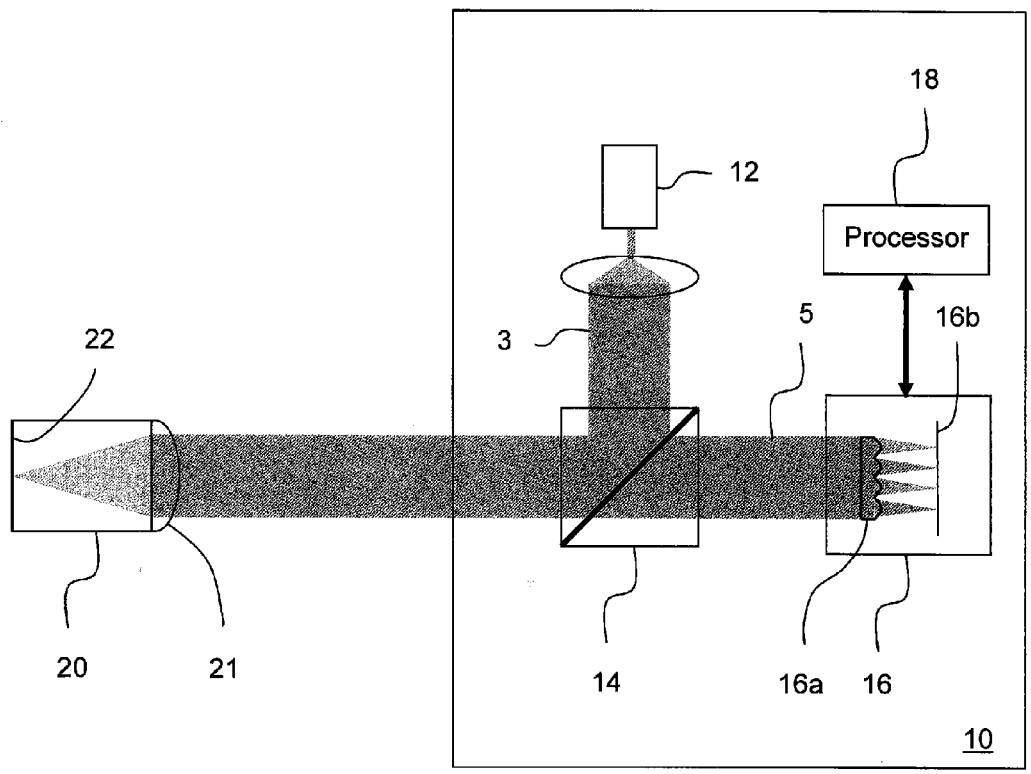
FIG. 2 illustrates an example of an optical measurement instrument which may make a measurement with one example embodiment of a model eye to verify correct operation and specified performance of the optical measurement instrument.

FIG. 2 illustrates an example of an optical measurement instrument 10 making a measurement with one example embodiment of a model eye 20 to verify correct operation and specified performance of an optical measurement instrument. Here optical measurement instrument 10 may be a wavefront aberrometer. Optical measurement instrument 10 includes, among other elements, a coherent light source (e.g., a laser or SLD) 12, a beamsplitter 14, a wavefront sensor 16, and a processor 18. In some embodiments wavefront sensor 16 may be a Shack-Hartmann wavefront sensor including a lenslet array 16a and a pixel array 16b (e.g., camera, charge-coupled-device (CCD) or CMOS array). In various embodiments, optical measurement instrument 10 may include a variety of other elements not shown in FIG. 1, such as optical elements (e.g., lenses, mirrors, etc.), a fixation target, aperture stops, etc. Model eye 20 has a front surface 21 and a rear or back surface 22. Front surface 21 may be curved to focus light onto rear surface 22 such that front surface 21 acts as a "lens" for model eye 20, and rear surface 22 acts as a "retina" for model eye 20.

To verify that optical measurement instrument 10 is performing correctly, coherent light source 12 generates a probe beam 3 which is injected into front surface 21 of model eye 20. Light scatters from rear surface 22 of model eye 20 and some of the scattered light travels back out of front surface 21 and into optical measurement instrument 10 as a return beam 5. Return beam 5 is provided to wavefront sensor 16 which can operate with processor 18 to make one or more measurements of one or more characteristics of model eye 20. The measurement(s) can be compared with known or previously measured characteristics of model eye 20 to allow a determination to be made as to whether optical measurement instrument 10 is operating correctly and/or within its specified performance tolerances.

As noted above, in general return beam 5 will exhibit a speckle pattern with some bright-to-dark ratio. If the bright-to-dark ratio of the speckle pattern is too great, then the measurement(s) of model eye 20 may be subject to error that may make it difficult to impossible to verify proper operation of optical measurement instrument 10.

Various techniques may be employed to address the problem of a speckle pattern whose bright-to-dark ratio is too great. The exterior of rear surface 22 of model eye 20 may be painted to make the reflectivity approximate that of the human eye. However it has been observed that generally, a painted surface also causes excessive speckle. Another solution is simply to turn up the power on light source 12 so the dark regions at least get some light. However, this does not solve the problem of calculated wavefront errors caused by intensity coupling as described above. Another solution is to send probe beam 3 through a rotating disk that moves the beam slightly on back surface 22 of model eye 20 during the time that pixel array 16b of wavefront sensor 16 is acquiring an image. This moves the speckle pattern around during the acquisition and fills in the dark regions. However, this adds complexity to the system. Another similar solution is to move back surface 22 of model eye 20 slightly during the acquisition time. This can be done by gently tapping on model eye 20. However that is not a practical solution for many reasons. Another possibility is to vibrate model eye 20 by some more controlled means, such as with an ultrasonic transducer. However that would require an energy source for model eye 20, such as a battery, again adding complexity to the system.

Figure 3A:
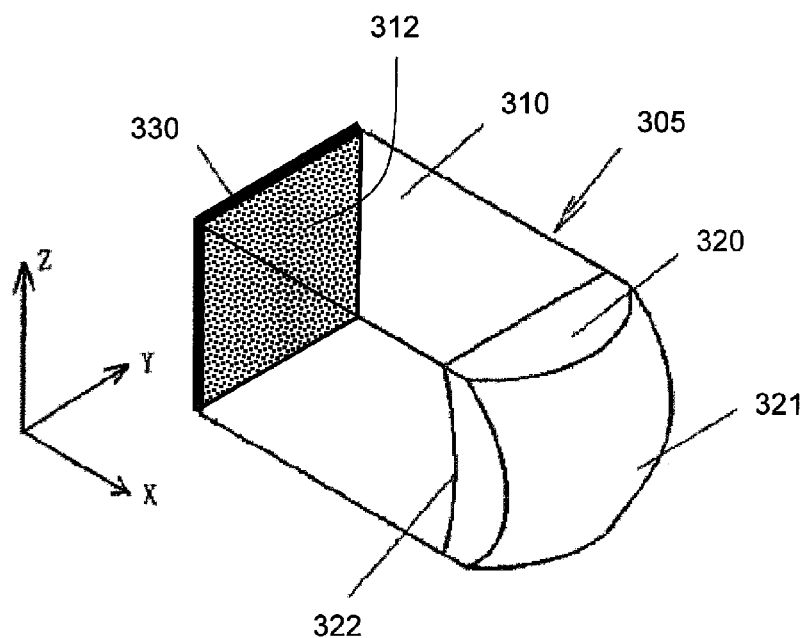
FIGS. 3A-3B illustrate one example embodiment of a model eye.
Figure 3B:
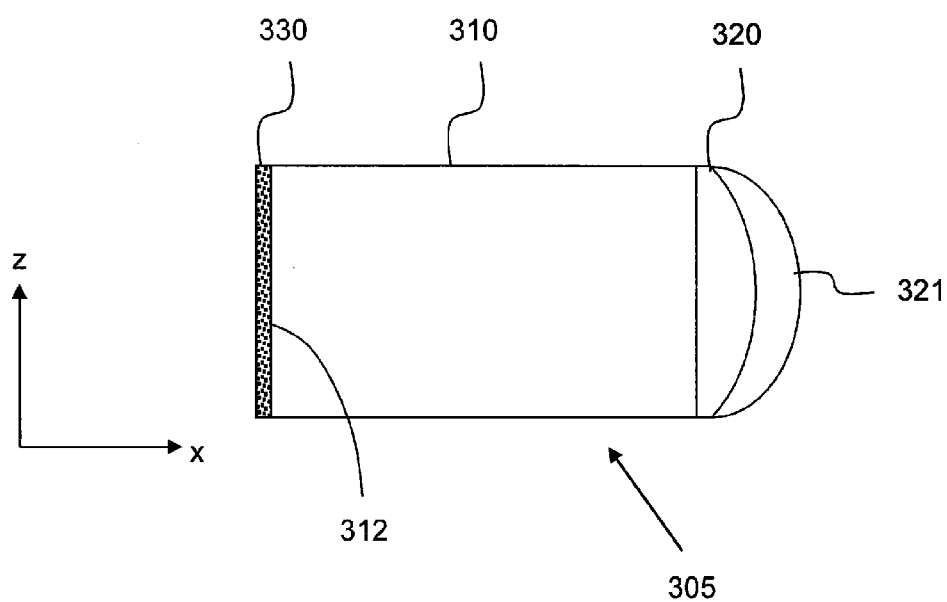

FIGS. 3A-3B illustrate one example embodiment of a model eye 300 that can produce a speckle pattern with a reduced bright-to-dark ratio. Model eye 300 includes an optically transmissive structure 305 having a front surface 321 and an opposite rear or back surface 312; and a material structure 330 adhered to rear surface 312 of optically transmissive structure 305.

Front surface 321 may be curved to focus light onto the opposite rear surface 312, which may be planar, such that front surface 321 acts as a "lens" for model eye 300, and rear surface 312 acts as a "retina" for model eye 300.

In some embodiments, optically transmissive structure 305 may comprise glass or a transparent polymer. In model eye 300, optically transmissive structure 305 includes a first plano-cylindrical portion 310 and a second sphero-cylindrical portion 320 which meet at a plano interface 322. In optically transmissive structure 305, first plano-cylindrical portion 310 and second sphero-cylindrical portion 320 may be formed as a unitary structure, or may comprise two separate structures joined together at the plano interface 322. Also, in other embodiments the optically transmissive structure of a model eye may have a different shape, for example a cylindrical structure with a circular cross-section instead of the rectangular or square cross-section of optically transmissive structure 305.

When used to verify the proper operation of an optical measurement instrument (e.g., optical measurement instrument 10), front curved surface 321 of optically transmissive structure 305 receives a coherent light beam and provides it to the opposite rear surface 312, and rear surface 312 directs a portion of the coherent light beam back out through front surface 321.

Beneficially, material structure 330 has a characteristic to cause a speckle pattern of the portion of the coherent light beam that is directed back out through front surface 321 of optically transmissive structure 310 to have a reduced bright-to-dark ratio compared to the bright-to-dark ratio of the speckle pattern that is produced in the absence of material structure 330. Beneficially, material structure 330 has a characteristic to cause a speckle pattern of the portion of the coherent light beam that is directed back out front surface 321 of optically transmissive structure 310 to have a bright-to-dark ratio of less than 2:1.

FIGS. 4A-4E illustrate some example embodiments of the material structure 330 of FIGS. 3A-B.

Figure 4A:
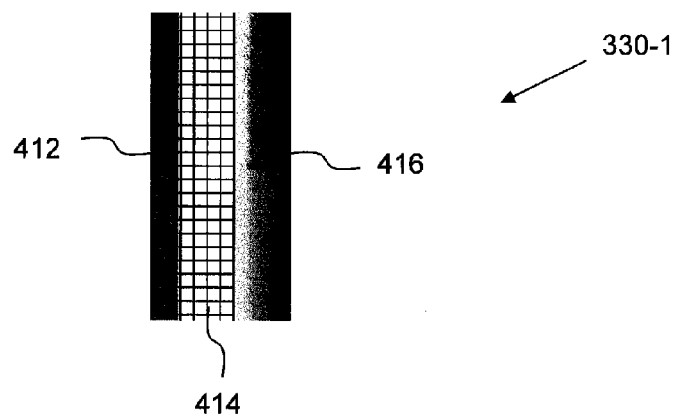
FIGS. 4A-4E illustrate some example embodiments of a material structure that may be applied to a back surface of an optically transmissive structure of a model eye.

FIG. 4A illustrates a first embodiment 330-1 of material structure 330 comprising a piece of duct tape.

Generally speaking, duct tape is a fabric-reinforced polyethylene pressure-sensitive tape with a semi-flexible shell and a pressure-sensitive adhesive. Duct tape was first marketed around 1942 and its first large scale use was by the U.S. military, for example to keep moisture out of ammunition cases. Commonly, duct-tape construction consists of a polyisoprene-based adhesive 414, a fabric (scrim) reinforcement 414, and a polyethylene backing 416.

Surprisingly, the inventor has discovered that by adhering a piece of duct tape to the rear surface of the optically transmissive structure of a model eye, the speckle pattern of the light returned from the rear surface of the optically transmissive structure and back out the front surface of the optically transmissive structure has a speckle pattern which exhibits a reduced bright-to-dark ratio compared to the same model eye without the duct tape. In some embodiments, the speckle pattern exhibits a bright-to-dark ratio of less than or equal to 2:1. In some embodiments, so-called gaffer tape may be employed in lieu of duct tape.

Figure 4B:
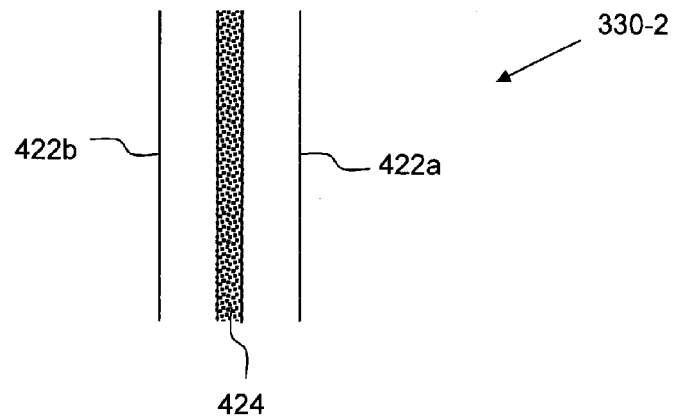

FIG. 4B illustrates a second embodiment 330-2 of material structure 330 comprising at least two layers 422a & 422b of optically transmissive adhesive tape with a material 424 having a plurality of light scattering particles disposed between the at least two layers of optically transmissive adhesive tape. By adhering material structure 330-2 to the rear surface of the optically transmissive structure of a model eye, the speckle pattern of the light returned from the rear surface of the optically transmissive structure and back out the front surface of the optically transmissive structure has a speckle pattern which exhibits a reduced bright-to-dark ratio compared to the same model eye without material structure 330-2. In some embodiments, the speckle pattern exhibits a bright-to-dark ratio of less than or equal to 2:1.

Figure 4C:
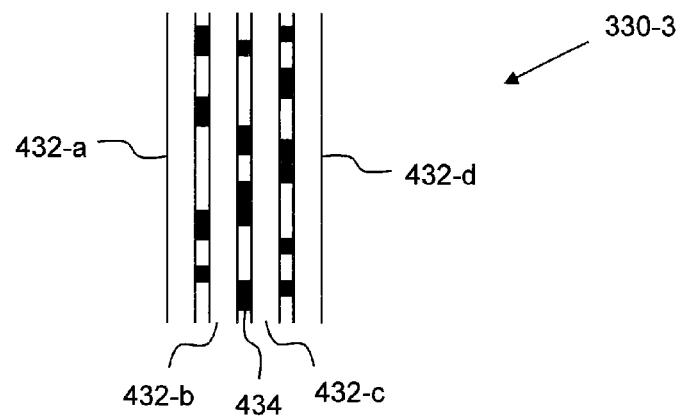

FIG. 4C illustrates a third embodiment 330-3 of material structure 330 comprising a plurality of layers 432a, 432b, 432c & 432d of optically transmissive adhesive tape with a plurality of pencil or graphite marks 434 on each successive layer of the optically transmissive adhesive tape. By adhering material structure 330-3 to the rear surface of the optically transmissive structure of a model eye, the speckle pattern of the light returned from the rear surface of the optically transmissive structure and back out the front surface of the optically transmissive structure has a speckle pattern which exhibits a reduced bright-to-dark ratio compared to the same model eye without material structure 330-3. In some embodiments, the speckle pattern exhibits a bright-to-dark ratio of less than or equal to 2:1.

Figure 4D:
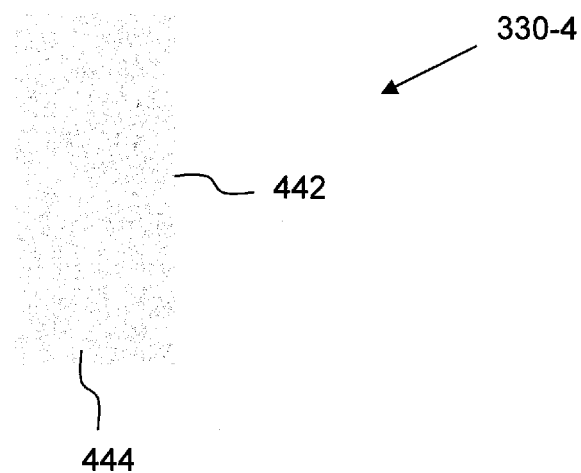

FIG. 4D illustrates a fourth embodiment 330-4 of material structure 330 comprising a layer of optically transmissive paint 442 with light scattering particles 444 embedded within. By adhering material structure 330-4 to the rear surface of the optically transmissive structure of a model eye, the speckle pattern of the light returned from the rear surface of the optically transmissive structure and back out the front surface of the optically transmissive structure has a speckle pattern which exhibits a reduced bright-to-dark ratio compared to the same model eye without material structure 330-4. In some embodiments, the speckle pattern exhibits a bright-to-dark ratio of less than or equal to 2:1.

Figure 4E:
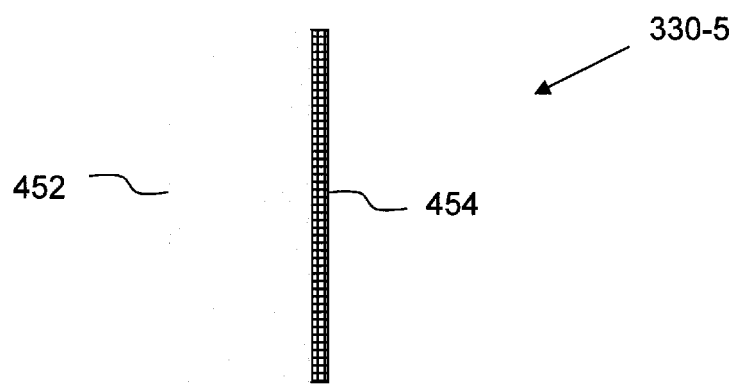

FIG. 4E illustrates a fifth embodiment 330-5 of material structure 330 comprising a caulking material 452 with a gauze material 454 applied thereto. By adhering material structure 330-5 to the rear surface of the optically transmissive structure of a model eye, the speckle pattern of the light returned from the rear surface of the optically transmissive structure and back out the front surface of the optically transmissive structure has a speckle pattern which exhibits a reduced bright-to-dark ratio compared to the same model eye without material structure 330-5. In some embodiments, the speckle pattern exhibits a bright-to-dark ratio of less than or equal to 2:1.

Although FIGS. 4A-4E show various specific embodiments of material structures of material structure 330, it should be understood that other embodiments are possible. In some other embodiments, the material structure may be otherwise incorporated (e.g., painted, sprayed, extruded, thermoformed, or the like) into the model eye such that the material structure is located at or on the rear surface of the optically transmissive structure of the model eye and provide the characteristic of causing the light received by the measurement instrument from the rear surface of the optically transmissive structure to have a speckle pattern with a reduced bright-to-dark ratio, and beneficially a bright-to-dark ratio of less than 2:1.

Figure 5:
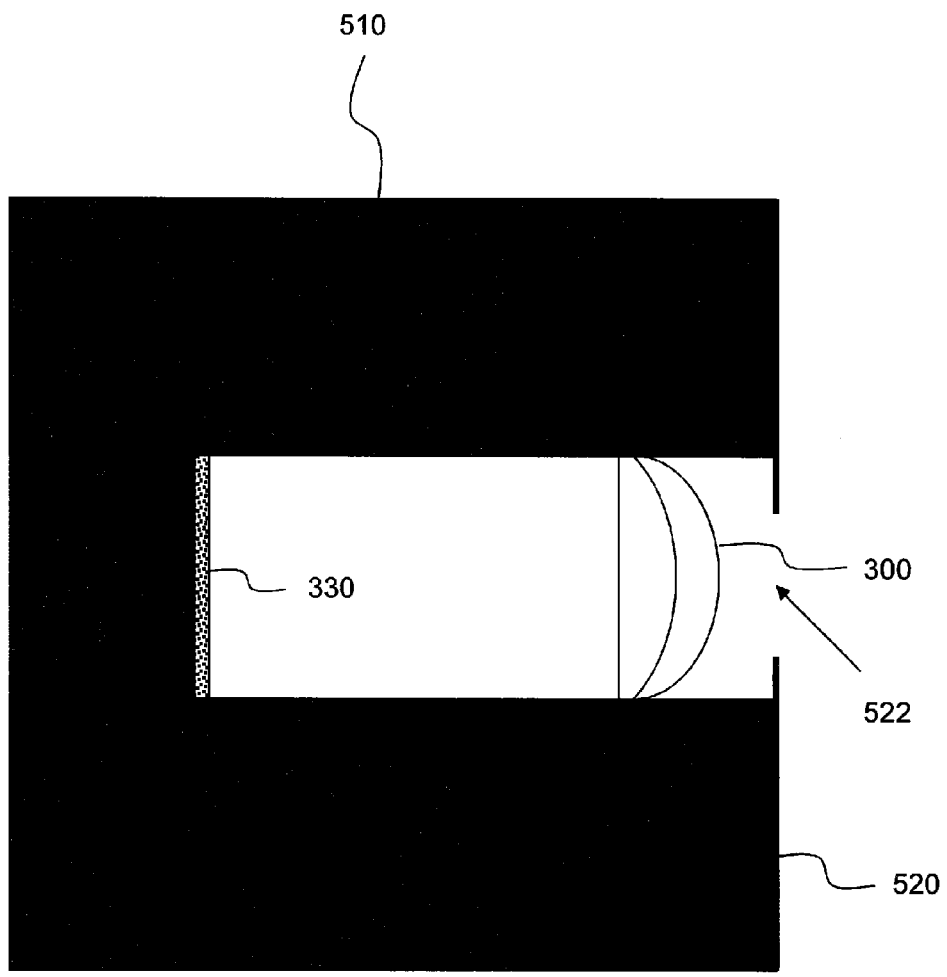
FIG. 5 illustrates another example embodiment of a model eye.

FIG. 5 illustrates another example embodiment of a model eye 500. Model eye 500 includes model eye 300 of FIGS. 3A-3B, together with a model eye holder or mount 510, and an opaque structure 520 having an aperture 522 therethrough disposed in front of the front surface of model eye 300. Opaque structure 520 may act as an "iris" for model eye 500. The operation of model eye 500 is similar to that of model eye 300 and so a description thereof will not be repeated.

Figure 6:
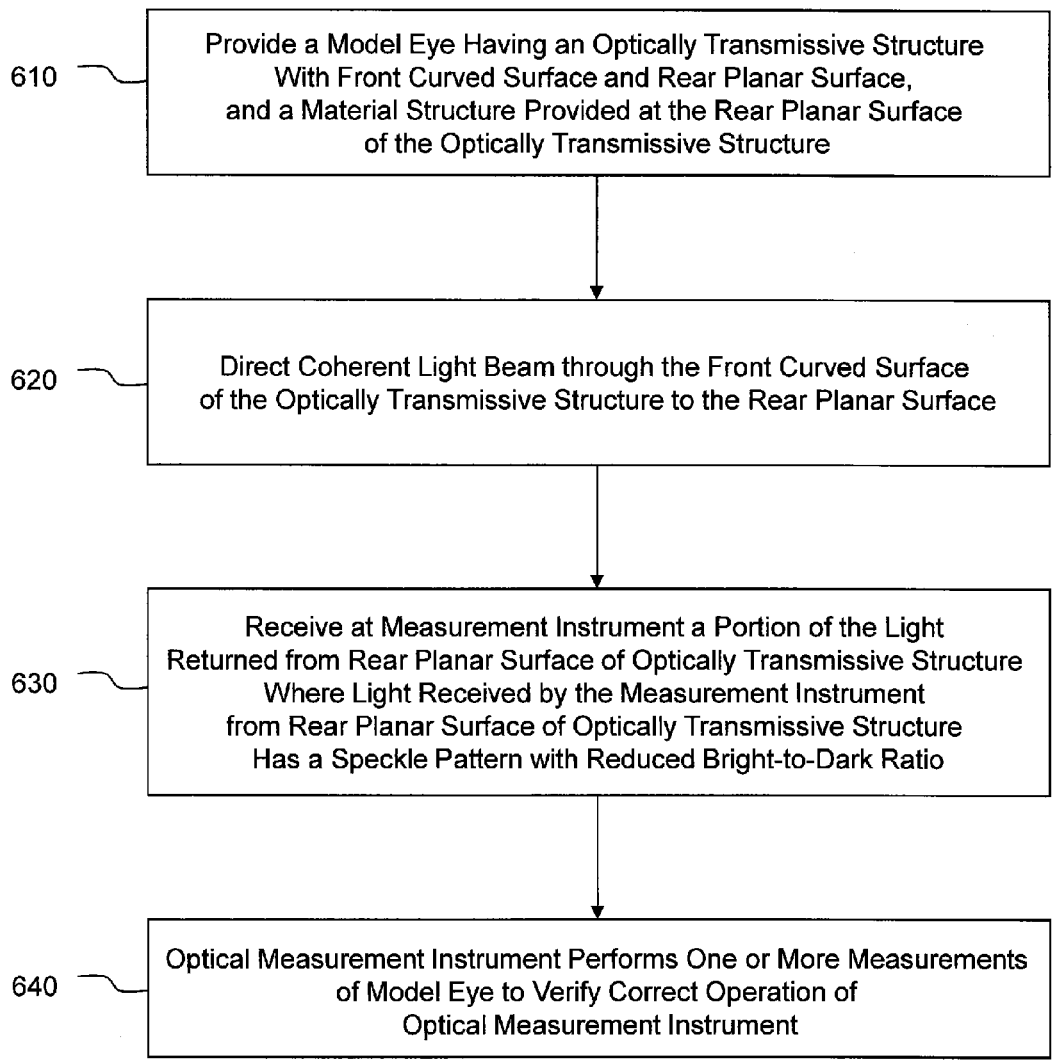
FIG. 6 is a flowchart of an example embodiment of a method for verifying proper operation and performance of optical measurement equipment.

FIG. 6 is a flowchart of an example embodiment of a method 600 for verifying proper operation and performance of optical measurement equipment.

In operation 610, a model eye is provided as an optically transmissive structure with a front curved surface and a rear planar surface, and a material structure provided at (e.g. adhered to) the rear planar surface of the optically transmissive structure. The model eye may be model eye 300 or model eye 500, and the material structure may be material structure 330, including for example any of the embodiments shown in FIGS. 4A-4E.

In operation 620, a coherent light beam is directed through the front curved surface of the optically transmissive structure to the opposite rear planar surface.

In operation 630, a measurement instrument receives a portion of the light returned from the rear planar surface of the optically transmissive structure. The material structure has a characteristic to cause the light received by the measurement instrument from the rear planar surface of the optically transmissive structure to have a speckle pattern with a reduced bright-to-dark ratio, and beneficially a bright-to-dark ratio of less than 2:1.

In operation 640, the optical measurement instrument performs one or more measurements of the model eye to verify correct operation of the optical measurement instrument, for example by comparing the measurement result(s) to known parameters of the model eye.

In some embodiments, as discussed in greater detail below, where the optical measurement instrument include an optical coherence tomographer (OCT), the measurements may include a measurement of a thickness (i.e., the x direction in FIGS. 3A-B) of the material structure provided at the rear planar surface of the optically transmissive structure of the model eye. In that case, the measured thickness may be compared to a known thickness of the material structure (e.g., a thickness previously measured to be correct) as part of an operation of verifying correct operation of the optical measurement instrument. That is, if the thickness of the material structure as measured by an OCT of the measurement instrument does not agree with the predetermined or known thickness of the material structure (which may be stored within a memory device of the optical measurement instrument) within some predetermined tolerance, then it may be determined that the optical measurement instrument is not operating properly within specifications. In other embodiments as described in greater detail below, instead of measuring the total thickness of the material structure, the material structure may have a plurality of layers, and the thicknesses of one or more of the individual layers may be measured. In other embodiments as described in greater detail below, the material structure may include a plurality of embedded fibers or other optically recognizable structure(s), and one or more dimensions of one or more embedded fibers or other optically recognizable structure(s) may be measured.

The embodiments of a model eye and methods described above may provide benefits and have wider applicability beyond the context of the optical measurement instrument 10 of FIG. 2. For example, the model eye and a method of using the model eye to verify proper operation of an optical measurement instrument may be applied to an optical measurement instrument which is employed for LASIK planning, an optical measurement instrument which performs cataract diagnostics or pre-operational cataract treatment planning, which may include specification and/or selection of an appropriate intraocular lens (IOL) for a particular patient, and/or post-surgical test and evaluation after an IOL has been implanted, etc.

Embodiments of one or more of such optical measurement instruments may include multiple eye measurement subsystems in one instrument, including an aberrometer (e.g., including a Shack-Hartmann wavefront sensor), a corneal topographer, and an optical coherence tomographer (OCT), for example in an integrated optical measurement instrument.

Figure 7:
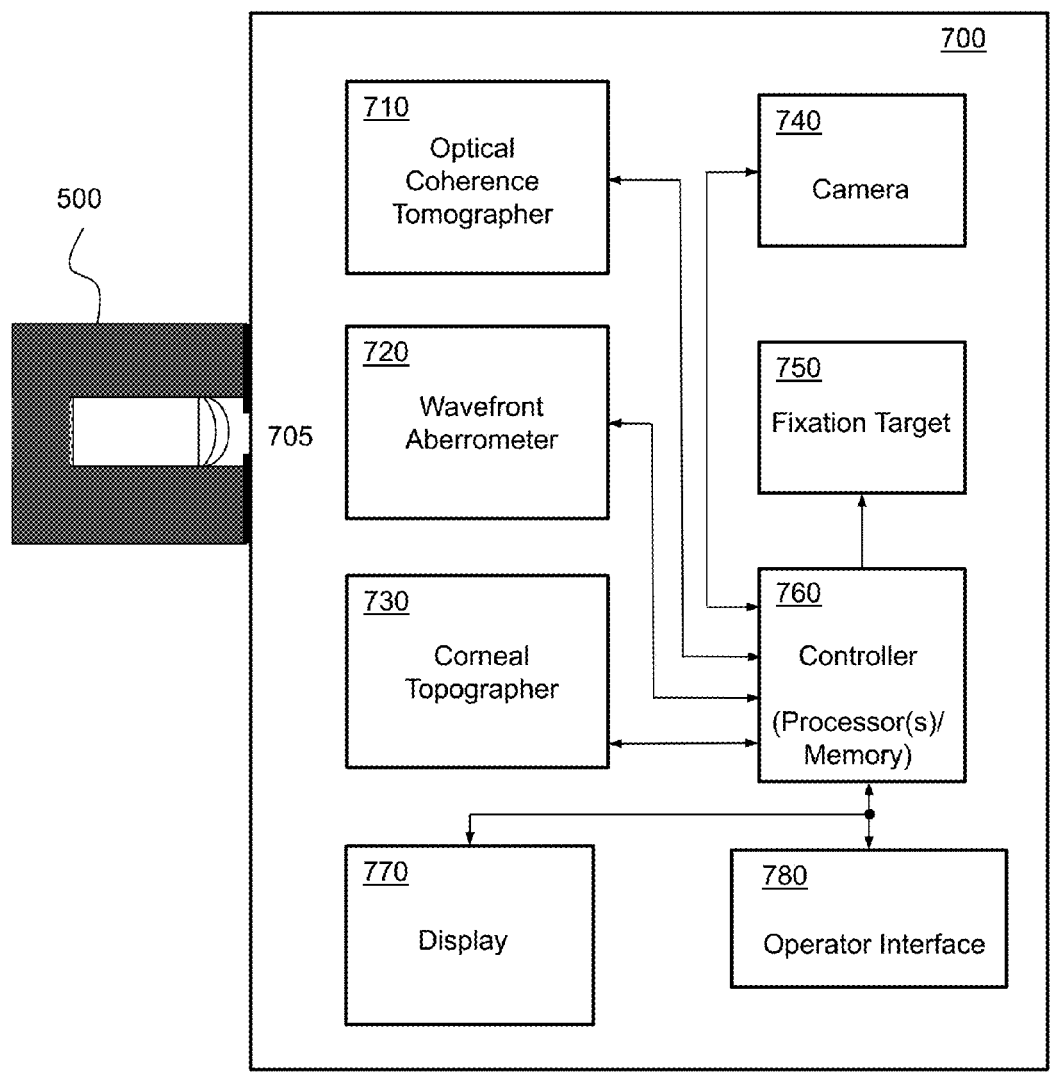
FIG. 7 is a block diagram of a system including an optical measurement instrument, and a model eye according to one or more embodiments described herein which may be used by the optical measurement instrument to verify correct operation and specified performance of the optical measurement instrument.

FIG. 7 is a block diagram of a system including an optical measurement instrument 700 and a model eye (e.g., model eye 300 or model eye 500) according to one or more embodiments described herein which may be used by optical measurement instrument 700 to verify correct operation and specified performance of optical measurement instrument 700.

Optical measurement instrument 700 includes: an optical coherence tomographer (OCT) subsystem 710, a wavefront aberrometer subsystem 720, and a corneal tomographer subsystem 730 for measuring one or more characteristics of a subject's eye. Optical measurement instrument 700 may further includes a camera 740, a fixation target 750, a controller 760, including one or more processor(s) and memory, a display 770 and an operator interface 780. Optical measurement instrument 700 further includes a patient interface 705 for a subject to present his or her eye for measurement by optical measurement instrument 700.

Optical coherence tomographer subsystem 710 is one example of an eye structure imaging subsystem which may be employed in optical measurement instrument 700. In other embodiments, a different eye structure imaging subsystem may be employed, for example a Scheinplug Imager, a fluorescence imager, a structured lighting imager, a wavefront tomographer, and an ultrasound imager.

In some embodiments, wavefront aberrometer 720 may comprise a Shack-Hartmann wavefront sensor as is known in the art.

In some embodiments, optical coherence tomographer subsystem 710, wavefront aberrometer subsystem 720, and corneal tomographer subsystem 730 may have a common fixation axis, and each subsystem may be operatively coupled to the others via controller 760.

In some embodiments, one or more processors of controller 760 may be configured to control optical measurement instrument 700 to execute various algorithms as described below.

In some embodiments, optical measurement instrument 700 may be configured to measure a plurality of characteristics of a subject's eye, including some or all of the following: ocular biometry information, anterior corneal surface information, posterior corneal surface information, anterior lens surface information, posterior lens surface information, lens tilt information and lens position information. In some embodiments, the ocular biometry information may include a plurality of central corneal thicknesses (CCT), an anterior chamber depth (ACT), a pupil diameter (PD), a white to white distance (WTW), a lens thickness (LT), an axial length (AL) and a retinal layer thickness. This measurement data may be stored in memory associated with controller 760.

In some embodiments, memory associated with controller 760 may store intraocular lens (IOL) model data for a plurality of IOL models, each of the IOL models having associated with it a plurality of predetermined parameters selected from the group consisting of dioptic power, refractive index, asphericity, toricity, haptic angulation and lens filter. The IOL data may be used by one or more processors of optical measurement instrument 700, in conjunction with measurement data of a subject's eye obtained by optical measurement instrument 700, for cataract diagnostics or cataract treatment planning, which may include specifying and/or selecting a particular IOL for a subject's eye. For example, one or more processors of optical measurement instrument 700 may execute an algorithm which includes: accessing the plurality of IOL models stored in, and for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL for the subject's eye from the plurality of IOL models corresponding to the optimized IOL based on a predetermined criteria.

In some embodiments, one or more processors of optical measurement instrument 700 may execute an algorithm comprising: determining a desired postoperative condition of the subject's eye; empirically calculating a post-operative condition of the eye based at least partially on the measured eye characteristics; and predictively estimating, in accordance with an output of said empirically calculating and the eye characteristics, at least one parameter of an intraocular lens for implantation into the subject's eye to obtain the desired postoperative condition.

Beneficially, during an instrument verification or calibration operation, model eye 500 may be provided at patient interface 705 and optical measurement instrument 700 may perform one or more measurements of model eye 500 to verify correct operation and specified performance of optical measurement instrument 700, as described above.

In particular, in some embodiments the one or more measurements may include optical coherence tomographer (OCT) subsystem 710 making a measurement of a thickness (x dimension in FIGS. 3A-3B) of the material structure 330 provided at rear planar surface 312 of optically transmissive structure 310 of model eye 300 or 500. In that case, the measured thickness may be compared to a known (e.g., previously correctly measured) thickness of material structure 330 as part of an operation of verifying correct operation of optical measurement instrument 700. In some embodiments, controller 760 may perform this comparison. That is, if the thickness of material structure 330 as measured by OCT subsystem 710 of optical measurement instrument 700 does not agree with the known thickness of material structure 330 (which may be stored within a memory device of controller 760 of optical measurement instrument 700) within some specified tolerance, then controller 760 may determine that optical measurement instrument 700 is not operating properly within specifications. In that case, a notification or alert to that effect may be provided to an operator of optical measurement instrument 700, for example via controller 760 causing display 770 to display to such a notification or alert to the operator.

In some embodiments where the material structure 330 comprises a multilayer structure, for example as illustrated in FIGS. 4A, 4B and 4C, optical coherence tomographer (OCT) subsystem 710 may measure the thickness of one or more of these layers and these thicknesses may be compared to the known thicknesses of these layers (which may be stored within a memory device of controller 760 of optical measurement instrument 700). If one or more of the measured thicknesses do not agree with the corresponding known thickness within some particular tolerance, then controller 760 may determine that optical measurement instrument 700 is not operating properly within specifications. Again, in that case, a notification or alert to that effect may be provided to an operator of optical measurement instrument 700, for example via controller 760 causing display 770 to display to such a notification or alert to the operator.

In some embodiments the material structure 330 may include a plurality of embedded fibers or other optically recognizable feature(s). In that case, optical coherence tomographer (OCT) subsystem 710 may measure one of more dimensions of these fibers or other optically recognizable structure(s), and compare the measured dimension(s) with corresponding known dimensions. As above, when the measured dimension(s) do not agree with corresponding known dimension(s) within some particular tolerance, then controller 760 may determine that optical measurement instrument 700 is not operating properly within specifications, and again a notification or alert to that effect may be provided to an operator of optical measurement instrument 700, for example via controller 760 causing display 770 to display to such a notification or alert to the operator.

Figure 8A:
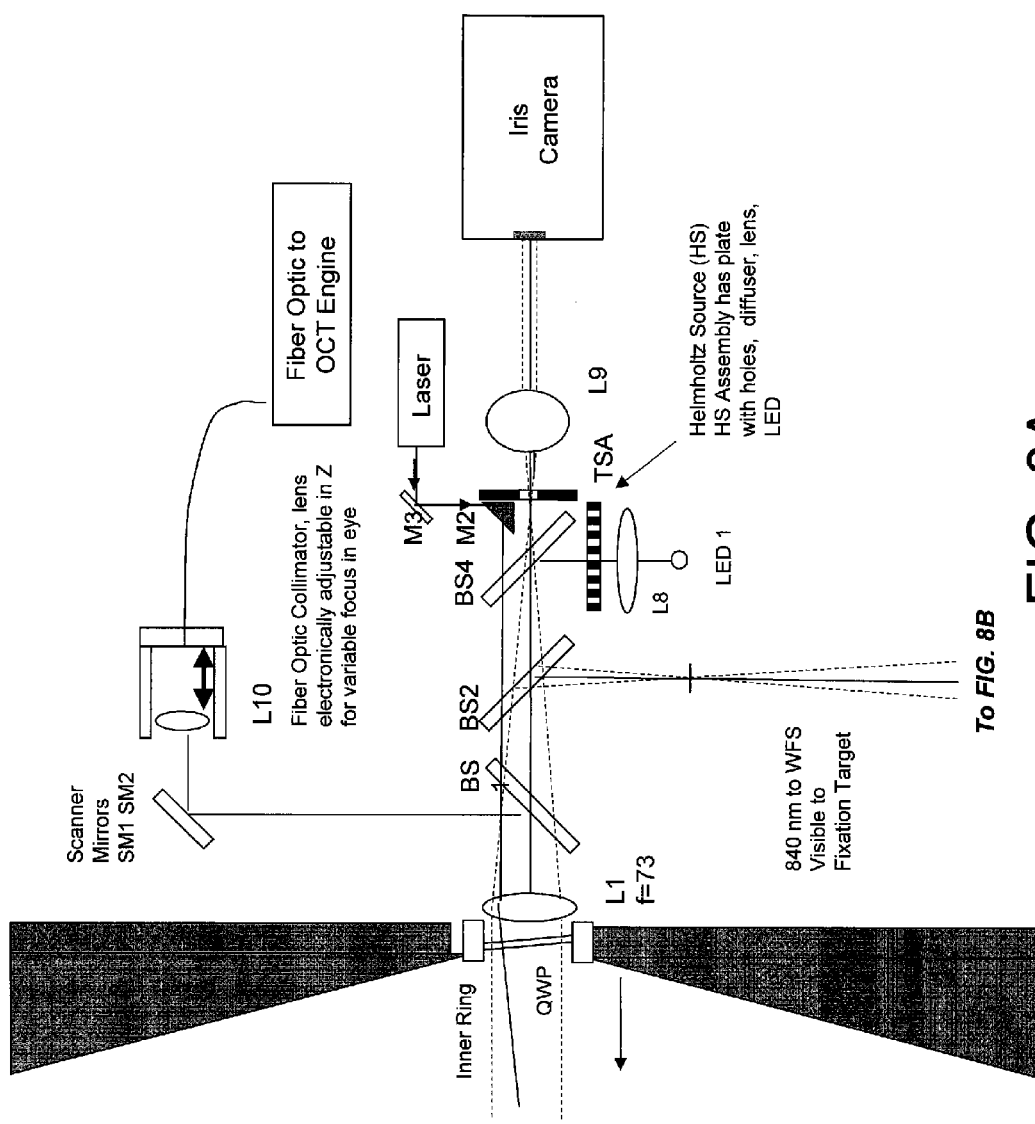
FIGS. 8A and 8B illustrate together an example of an optical measurement instrument according to the block diagram of FIG. 7.
Figure 8B:
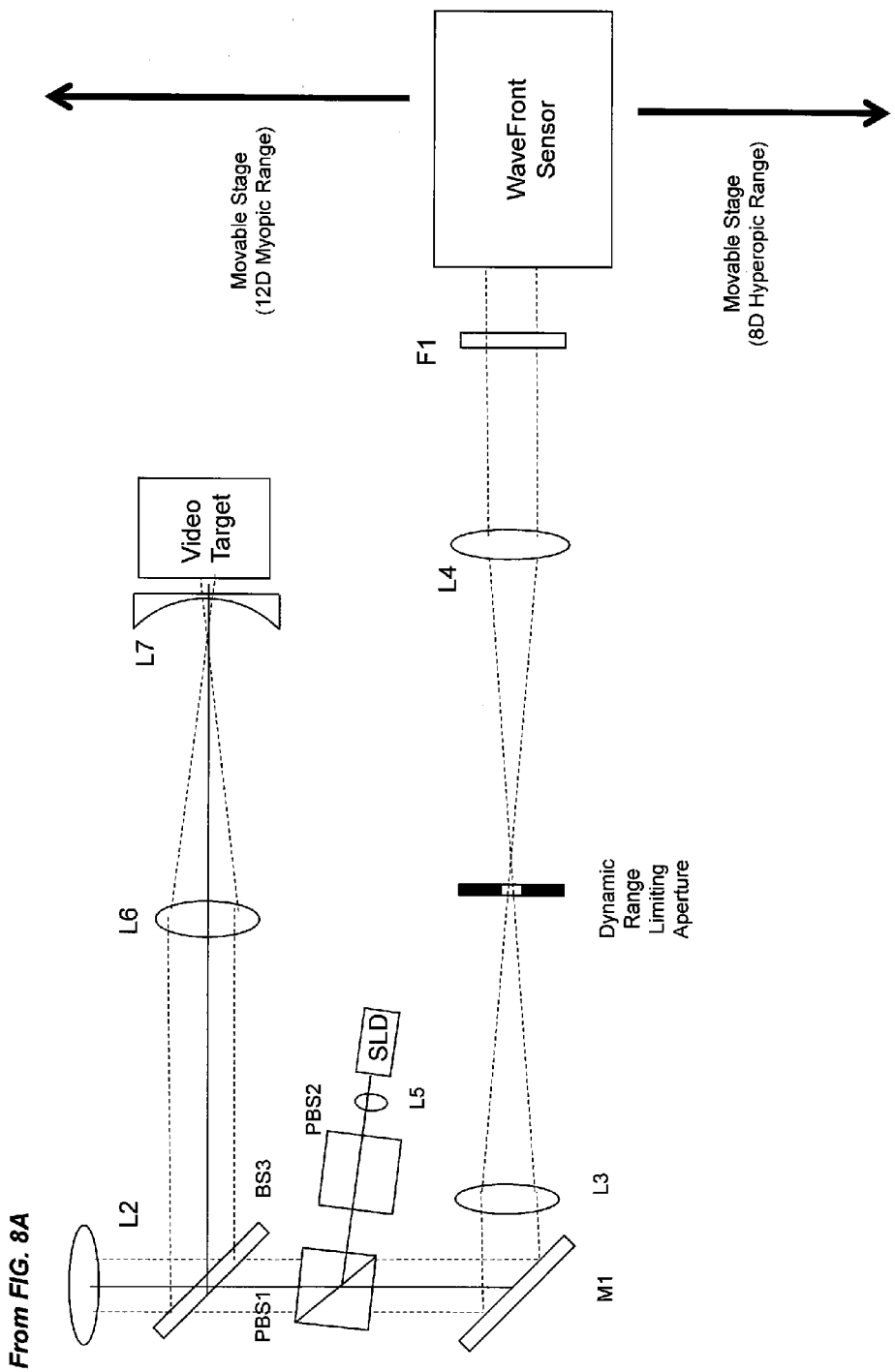

FIGS. 8A and 8B illustrate together an example of an optical measurement instrument 800 according to the block diagram of FIG. 7. In particular, FIG. 8A shows elements of an optical coherence tomographer subsystem, such as optical coherence tomographer subsystem 710 of FIG. 7, and elements of a corneal topographer subsystem, such as corneal topographer subsystem 730 of FIG. 7. FIG. 8B shows elements of a wavefront aberrometer subsystem, such as wavefront aberrometer 720 of FIG. 7, and a fixation target.

In particular, FIG. 8A shows an optical coherence tomographer subsystem with scanning mirrors SM1 and SM2 and a lens L10 whose focus can be changed to selectively focus the OCT measurements at different parts of a subject's eye (e.g., anterior corneal surface; posterior corneal surface; anterior lens surface; posterior lens surface; retinal surface; etc.). FIG. 8A also shows a corneal topographer subsystem with an inner ring light source and Helmholtz sources formed by an LED 1, a diffuser lens 8, and a plate with holes for passing the diffused light therethrough. FIG. 8A also shows an iris camera.

FIG. 8B shows a wavefront aberrometer subsystem, including a wavefront sensor and an adjustable telescope with a dynamic range limiting aperture disposed between the lenses of the adjustable telescope. Beneficially, the wavefront sensor and one of the telescope lenses may be mounted on a movable stage with can be adjusted to correct, for example, for up to 12 Dipoters in the myopic range and up to 8 Diopters in the hyperopic range. FIG. 8B also shows a superluminescent diode (SLD) as a light source for the wavefront aberrometer, and a fixation target in the visible light range, for example a video target.

In some embodiments, various subsystems of optical measurement instrument 800 may operate with light at different wavelengths. For example, in some embodiments: the optical coherence topographer subsystem may operate with light at a wavelength of about 1060 nm; the Helmholtz sources of the corneal topographer subsystem may operate at a wavelength of about 760 nm; the iris camera may use light at both 760 nm of the Helmholtz sources and at 950 nm; the fixation target may operate in a visible wavelength range of 500-600 nm; and the wavefront sensor may operate at a wavelength of about 840 nm.

Figure 9:
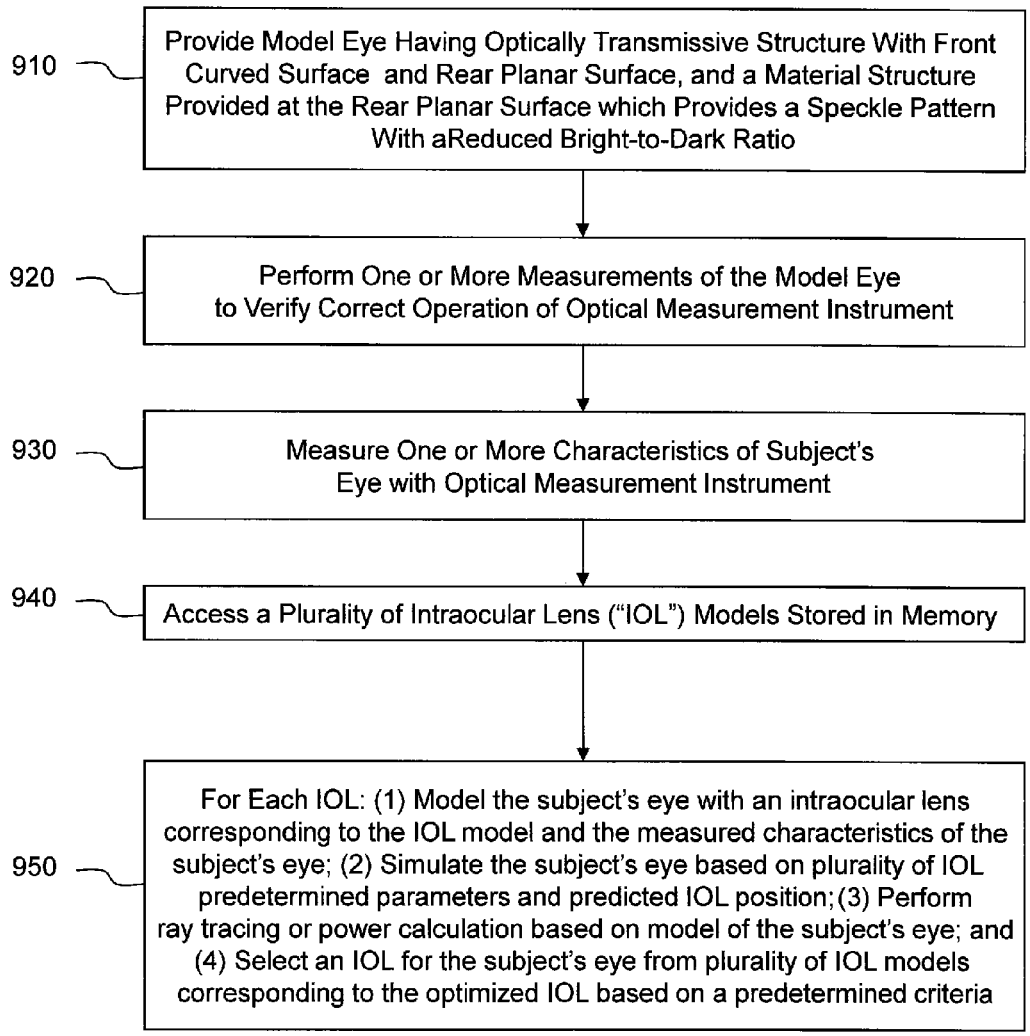
FIG. 9 is a flowchart of an example embodiment of a method for performing cataract diagnostics for an eye with an optical measurement instrument whose operation is verified using a model eye according to one or more embodiments described herein.

FIG. 9 is a flowchart of an example embodiment of a method 900 for cataract diagnostics for an eye with an optical measurement instrument whose operation is verified using a model eye according to one or more embodiments described herein.

An operation 910 includes providing a model eye having an optically transmissive structure with a front curved surface and a rear planar surface, and a material structure provided at the rear planar surface which provides a speckle pattern with a bright-to-dark ratio of less than 2:1.

An operation 920 includes performing one or more measurements of the model eye to verify correct operation of the optical measurement instrument.

In some embodiments, the measurements may include an optical coherence tomographer (OCT) subsystem measuring a thickness of the material structure provided at the rear planar surface of the optically transmissive structure of the model eye. In that case, the measured thickness may be compared to a known thickness of the material structure (e.g., a thickness previously measured to be correct) as part of an operation of verifying correct operation of the optical measurement instrument. That is, if the thickness of the material structure as measured by an OCT of the measurement instrument does not agree with the predetermined or known thickness of the material structure, within some particular tolerance, then it may be determined that the optical measurement instrument is not operating properly within specifications.

In some embodiments where the material structure comprises a multilayer structure, for example as illustrated in FIGS. 4A, 4B and 4C, an optical coherence tomographer (OCT) subsystem may measure the thickness of one or more of these layers and these thicknesses may be compared to the known thicknesses of these layers. That is, if one or more of the measured thicknesses do not agree with the corresponding known thickness within some particular tolerance, then it may be determined that the optical measurement instrument is not operating properly within specifications.

In some embodiments the material structure may include a plurality of embedded fibers or other optically recognizable feature(s). In that case, an optical coherence tomographer (OCT) subsystem may measure one of more dimensions of these fibers or other optically recognizable feature(s), and compare the measured dimension(s) with corresponding known dimension(s). In that case, when the measured dimension(s) do not agree with the known dimension(s) within some particular tolerance, then it may be determined that the optical measurement instrument is not operating properly within specifications.

An operation 930 includes measuring one or more characteristics of a subject's eye with the optical measurement instrument.

An operation 940 includes accessing a plurality of Intraocular Lens ("IOL") models stored in memory.

An operation 950 includes, for each IOL: (1) model the subject's eye with an intraocular lens corresponding to the IOL model and the measured characteristics of the subject's eye; (2) simulating the subject's eye based on a plurality of IOL predetermined parameters and a predicted IOL position; (3) performing ray tracing or power calculation based on model of the subject's eye; and (4) selecting an IOL for the subject's eye from the plurality of IOL models corresponding to the optimized IOL based on a predetermined criteria.

All patents and patent applications cited here are hereby incorporated by reference hereby reference in their entirety.

The use of the terms "a" and "an" and "the" and similar referents in the context of describing the invention (especially in the context of the following claims) are to be construed to cover both the singular and the plural, unless otherwise indicated here or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values here are merely intended to serve as a shorthand method of referring individually to each separate value falling within the range, unless otherwise indicated herein, and each separate value is incorporated into the specification as if it were individually recited herein. All methods described here can be performed in any suitable order unless otherwise indicated here or otherwise clearly contradicted by context. The use of any and all examples, or exemplary language (e.g., "such as") provided herein, is intended merely to better illuminate embodiments of the invention, and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made and remain within the concept without departing from the spirit or scope of the invention. Such variations would become clear to one of ordinary skill in the art after inspection of the specification, drawings and claims herein. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

We claim:

1. A method, comprising:
    providing a model eye comprising an optically transmissive structure having a front curved surface and an opposite rear planar surface, and a material structure provided at the rear planar surface of the optically transmissive structure having a characteristic to cause a speckle pattern of a portion of a coherent light beam that is directed back out through the front curved surface of the optically transmissive structure to have a bright-to-dark ratio of less than 2:1;
    performing one or more measurements of the model eye to verify correct operation of an optical measurement instrument which includes:
        a corneal topography subsystem,
        a wavefront sensor subsystem, and
        an eye structure imaging subsystem; and
    employing the optical measurement instrument to measure a plurality of characteristics of a subject's eye, comprising ocular biometry information, anterior corneal surface information, posterior corneal surface information, anterior lens surface information, posterior lens surface information, lens tilt information and lens position information.

2. The method of claim 1, wherein the eye structure imaging subsystem comprises an optical coherence tomography subsystem, and wherein performing one or more measurements of the model eye to verify correct operation of the optical measurement instrument includes:
    performing an optical coherence tomography measurement, with the optical coherence tomography subsystem, to measure a thickness of the material structure provided at the rear planar surface of the optically transmissive structure of the model eye;
    comparing the measured thickness to a known thickness of the material structure provided at the rear planar surface of the optically transmissive structure of the model eye; and
    when the measured thickness does not agree with the known thickness within a particular tolerance, determining that the optical measurement instrument is not operating properly within specifications.

3. The method of claim 1, wherein the material structure comprises a fabric-reinforced polyethylene pressure-sensitive tape adhered to the rear planar surface of the optically transmissive structure by an adhesive.

4. The method of claim 1, wherein the material structure comprises at least two layers of optically transmissive adhesive tape with a material having a plurality of light scattering particles disposed between the at least two layers of optically transmissive adhesive tape.

5. The method of claim 1, wherein the material structure comprises a plurality of layers of optically transmissive adhesive tape with a plurality of pencil marks on each successive layer of the optically transmissive adhesive tape.

6. The method of claim 1, wherein the material structure comprises a layer of optically transmissive paint with light scattering particles embedded within.

7. The method of claim 1, wherein the material structure comprises a caulking material with a gauze material applied thereto.

8. The method of claim 1, further comprising:
    determining a desired postoperative condition of the subject's eye;
    empirically calculating a post-operative condition of the eye based at least partially on the measured eye characteristics; and
    predictively estimating, in accordance with an output of said empirically calculating and the eye characteristics, at least one parameter of an intraocular lens for implantation into the subject's eye to obtain the desired postoperative condition.

9. The method of claim 1, wherein the ocular biometry information comprises a plurality of central corneal thicknesses (CCT), an anterior chamber depth (ACT), a pupil diameter (PD), a white to white distance (WTW), a lens thickness (LT), an axial length (AL) and a retinal layer thickness.

10. The method of claim 1, further comprising:
    accessing a plurality of Intraocular Lens (IOL) models stored in a memory accessible by the optical measurement instrument, each of the IOL models having associated with it a plurality of predetermined parameters selected from the group consisting of dioptic power, refractive index, asphericity, toricity, haptic angulation and lens filter; and
    for each of the IOL models:
        (1) modeling the subject's eye with an intraocular lens corresponding to the IOL model and the measured characteristics of the subject's eye;
        (2) simulating the subject's eye based on the plurality of IOL predetermined parameters and the predicted IOL position;
        (3) performing one of a ray tracing and a power calculation based on said model of the subject's eye; and (4) selecting an IOL for the subject's eye from the plurality of IOL models corresponding to the optimized IOL based on a predetermined criteria.

11. The method of claim 1, wherein the material structure provided at the rear planar surface of the optically transmissive structure of the model eye has a plurality of layers, wherein the eye structure imaging subsystem comprises an optical coherence tomography subsystem, and wherein performing one or more measurements of the model eye to verify correct operation of the optical measurement instrument includes:
performing an optical coherence tomography measurement, with the optical coherence tomography subsystem, to measure thicknesses of at least two of the layers of the material structure provided at the rear planar surface of the optically transmissive structure of the model eye;
comparing the measured thicknesses to known thicknesses of the at least two layers of the material structure provided at the rear planar surface of the optically transmissive structure of the model eye; and
when the measured thicknesses for the at least two layers do not agree with the known thicknesses of the at least two layers within a particular tolerance, determining that the optical measurement instrument is not operating properly within specifications.

12. A system, comprising:
a model eye, comprising:
an optically transmissive structure having a front curved surface and an opposite rear planar surface, and
a material structure provided at the rear planar surface of the optically transmissive structure and having a characteristic to cause a speckle pattern of a portion of a coherent light beam that is directed back out through the front curved surface of the optically transmissive structure to have a bright-to-dark ratio of less than 2:1; and
an optical measurement instrument which includes:
a corneal topography subsystem,
a wavefront sensor subsystem, and
an eye structure imaging subsystem,
wherein the subsystems have a common fixation axis, and each subsystem is operatively coupled to the others via a controller, and
wherein the optical measurement instrument is configured to perform one or more measurements of the model eye to verify correct operation of the optical measurement instrument for measuring one or more characteristics of a subject's eye.

13. The system of claim 12, wherein the material structure comprises a fabric-reinforced polyethylene pressure-sensitive tape adhered to the rear planar surface of the optically transmissive structure by an adhesive.

14. The system of claim 12, wherein the material structure comprises at least two layers of optically transmissive adhesive tape with a material having a plurality of light scattering particles disposed between the at least two layers of optically transmissive adhesive tape.

15. The system of claim 12, wherein the material structure comprises a plurality of layers of optically transmissive adhesive tape with a plurality of pencil marks on each successive layer of the optically transmissive adhesive tape.

16. The system of claim 12, wherein the material structure comprises a layer of optically transmissive paint with light scattering particles embedded within.

17. The system of claim 12, wherein the material structure comprises a caulking material with a cloth material applied thereto.

18. The system of claim 12, wherein the eye structure imaging subsystem comprises an optical coherence tomography subsystem.

19. The system of claim 18, wherein the optical coherence tomography subsystem is configured to perform an optical coherence tomography measurement to measure a thickness of the material structure provided at the rear planar surface of the optically transmissive structure of the model eye, wherein the controller is configured to compare the measured thickness to a known thickness of the material structure provided at the rear planar surface of the optically transmissive structure of the model eye, and when the measured thickness does not agree with the known thickness within a specified tolerance, determine that the optical measurement instrument is not operating properly within specifications.

20. The system of claim 18, wherein the material structure provided at the rear planar surface of the optically transmissive structure of the model eye has a plurality of layers, wherein the optical coherence tomography subsystem is configured to perform an optical coherence tomography measurement to measure thicknesses of at least two of the layers of the material structure provided at the rear planar surface of the optically transmissive structure of the model eye, wherein the controller is configured to compare the measured thicknesses to known thicknesses of the at least two layers of the material structure provided at the rear planar surface of the optically transmissive structure of the model eye, and when the measured thicknesses for the at least two layers do not agree with the known thicknesses of the at least two layers within a particular tolerance, determining that the optical measurement instrument is not operating properly within specifications.

21. The system of claim 12, further comprising a memory operable to store data acquired from each of the corneal topography subsystem, the wavefront sensor subsystem and the eye structure imaging subsystem, wherein the stored data includes a plurality of ocular biometry information, anterior corneal surface information, posterior corneal surface information, anterior lens surface information, posterior lens surface information, lens tilt information and lens position information.

22. The system of claim 12, further comprising a memory operable to store intraocular lens (IOL) model data for a plurality of IOL models, each of the IOL models having associated with it a plurality of predetermined parameters selected from the group consisting of dioptic power, refractive index, asphericity, toricity, haptic angulation and lens filter.

23. The system of claim 22, further comprising a processor configured to execute an algorithm comprising:
for each of the IOL models:
(1) modeling the subject's eye with an intraocular lens corresponding to the IOL model and the measured characteristics of the subject's eye;
(2) simulating the subject's eye based on the plurality of IOL predetermined parameters and the predicted IOL position;
(3) performing one of a ray tracing and a power calculation based on said model of the subject's eye; and
(4) selecting an IOL for the subject's eye from the plurality of IOL models corresponding to the optimized IOL based on a predetermined criteria.

24. The system of claim 12, further comprising a processor configured to execute an algorithm comprising:
  determining a desired postoperative condition of the subject's eye;
  empirically calculating a post-operative condition of the subject's eye based at least partially on the one or more measured characteristics of the subject's eye; and
  predictively estimating, in accordance with an output of said empirically calculating and the eye characteristics, at least one parameter of an intraocular lens for implantation into the subject's eye to obtain the desired postoperative condition.

25. A system, comprising:
a model eye, comprising:
  an optically transmissive structure having a front curved surface and an opposite rear planar surface, and
  a tape adhered to the rear planar surface of the optically transmissive structure by a pressure sensitive adhesive; and
an optical measurement instrument which includes:
  a corneal topography subsystem;
  a wavefront sensor subsystem; and
  an eye structure imaging subsystem,
wherein the subsystems have a common fixation axis, and each subsystem is operatively coupled to the others via a controller, and
wherein the optical measurement instrument is configured to perform one or more measurements of the model eye to verify correct operation of the optical measurement instrument for measuring one or more characteristics of a subject's eye.

26. The system of claim 25, wherein the model eye further comprises an opaque structure having an aperture therethrough disposed on an opposite side of the front curved surface of the optically transmissive structure as the rear planar surface of the optically transmissive structure.

27. The system of claim 25, wherein the optically transmissive structure comprises glass or a transparent polymer.

28. The system of claim 25, wherein the tape comprises a fabric-reinforced polyethylene tape with a pressure-sensitive adhesive.

29. The system of claim 25, wherein the tape comprises one of duct tape, gaffer tape, and a latex tape.

30. The system of claim 25, wherein the model eye further comprises a holder having an opening therein defining a sleeve configured to hold the optically transmissive structure.

* * * * *